(12) United States Patent
Kirkland et al.

(10) Patent No.: US 9,734,544 B2
(45) Date of Patent: Aug. 15, 2017

(54) INTEGRATING PRE-HOSPITAL ENCOUNTERS INTO AN ELECTRONIC MEDICAL RECORD

(71) Applicant: CERNER INNOVATION, INC., Kansas City, KS (US)

(72) Inventors: Kerry Kirkland, Liberty, MO (US); Jason Jonas, Lee's Summit, MO (US); Donna Cappo, Centerview, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 388 days.

(21) Appl. No.: 14/063,201

(22) Filed: Oct. 25, 2013

(65) Prior Publication Data

US 2015/0120324 A1    Apr. 30, 2015

(51) Int. Cl.
*G06Q 50/22* (2012.01)
*G06Q 50/24* (2012.01)
*G06Q 10/10* (2012.01)

(52) U.S. Cl.
CPC ............. *G06Q 50/24* (2013.01); *G06Q 10/10* (2013.01)

(58) Field of Classification Search
CPC ............................. G06Q 50/22; G06Q 50/24
See application file for complete search history.

(56) References Cited

U.S. PATENT DOCUMENTS

| 2005/0209770 | A1* | 9/2005 | O'Neill et al. ............... 701/117 |
| 2008/0021730 | A1* | 1/2008 | Holla et al. ...................... 705/2 |
| 2011/0210864 | A1* | 9/2011 | Tremonti ..................... 340/902 |

* cited by examiner

*Primary Examiner* — Maroun Kanaan
(74) *Attorney, Agent, or Firm* — Shook, Hardy & Bacon L.L.P.

(57) ABSTRACT

Methods, computer systems, and computer storage media are provided for integrating pre-hospital encounters into an electronic medical record (EMR). An electronic Situation-Background-Assessment-Recommendation (SBAR) tool is provided that guides a clinician to gather demographic information and encounter information. The demographic information associated with one or more patients is received via the SBAR tool. The encounter information is received via the SBAR tool. At least a portion of the demographic information and the encounter information is communicated via the SBAR tool, while in transit via an emergency vehicle, to a healthcare facility. The demographic information and the encounter information are integrated into an EMR associated with each patient.

19 Claims, 9 Drawing Sheets

FIG. 7.

SBAR

710 — SITUATION
I AM CONCERNED ABOUT: MIKE GONZOLES
THE PATIENT CODE STATUS IS: FULL CODE
I AM CONCERNED ABOUT THE PATIENT'S STATUS:
(SELECT ALL THAT APPLY)

☐ RESPIRATORY    ☐ NEUROLOGICAL
☐ CARDIOVASCULAR ☐ OTHER           } 712
☐ INTEGUMENTARY

720 — BACKGROUND

ABNORMAL VITALS + ▼
LAST 7 DAYS

| | LATEST | PREVIOUS | PREVIOUS |
|---|---|---|---|
| TEMP | ↑39 06/15/10 1:00 | 37 06/15/10 1:00 | 37 06/15/10 1:00 |
| BP | ↑190/110 06/15/10 1:00 | 190/110 06/15/10 1:00 | 130/110 06/15/10 1:00 |
| RR | 15 06/15/10 1:00 | :10 06/15/10 1:00 | :10 06/15/10 1:00 |
| RR | ↓98 06/15/10 1:00 | ↓95 06/15/10 1:00 | ↓97 06/15/10 1:00 |

ABNORMAL VITALS + ▼
LAST 7 DAYS

| | LATEST | PREVIOUS | PREVIOUS |
|---|---|---|---|
| WBC | ↓4.0 06/15/10 1:00 | 6.5 06/15/10 1:00 | ↓4.0 06/15/10 1:00 |
| SODIUM | ↑145 06/15/10 1:00 | 140 06/15/10 1:00 | 140 06/15/10 1:00 |
| BUN | ↑6.0 06/15/10 1:00 | 8.0 06/15/10 1:00 | 8.0 06/15/10 1:00 |
| CREATININE | ↑3.0 06/15/10 1:00 | 1.0 06/15/10 1:00 | 1.0 06/15/10 1:00 |

ASSESSMENT — 730
I HAVE ASSESSED THE PATIENT, I THINK THE PROBLEM IS: (SELECT ALL THAT APPLY)

☐ RESPIRATORY RATE      ☐ SKIN COLOR
☐ OXYGEN SATURATION     ☐ LEVEL OF CONSCIOUS
☐ BREATH SOUNDS         ☐ ORIENTATION            } 732
☐ CARDIAC RHYTHM        ☐ AFFECT/BEHAVIOR
☐ PULSE RATE            ☐ BLOOD GLUCOSE
☐ BLOOD PRESSURE        ☐ URINE OUTPUT
☐ TEMPERATURE           ☐ ACTIVE BLEEDING

RECOMMENDATION — 740
RECOMMENDATIONS FOR THIS PATIENT: (SELECT ALL THAT APPLY)

I CONTACTED:
RECOMMENDED PROTOCOLS FOR THIS PATIENT: — 750
- INITIATE PROTOCOL(S) - ▼  — 752

☐ ABGS                    ☐ EKG
☐ BASIC METABOLIC PANEL   ☐ INCREASE VITALS FR.
☐ BLOOD CULTURES          ☐ URINE CULTURE
☐ CHEST XR                ☐ O2 THERAPY              } 754
☐ COMPLETE BLOOD COUNT    ☐ CONSULT
☐ CT SCAN                 ☐ CALL BACK
☐ DISCUSS CODE STATUS     ☐ TRANSFER TO
☐ ELECTROLYTE PANEL       ☐ OTHER

INTEGRATING PRE-HOSPITAL ENCOUNTERS INTO AN ELECTRONIC MEDICAL RECORD

BACKGROUND

Many patients are transported to hospitals via ambulances, helicopters, and other emergency vehicles. Information captured during these transports, if any, is fractured and does not get directly communicated to an electronic medical record (EMR). A lack of an electronic version of a Situation-Background-Assessment-Recommendation (SBAR) tool integrated into the EMR exacerbates this breakdown in communication. Further, there is not a useable EMR for the emergency medical services (EMS) market that is accessible via a tablet platform. Any information that is available is typically faxed or provided orally to a healthcare facility when communication protocols are available. Still further, ancillary conditions can negatively affect transport time, resources available, and benchmarks that define time limits on treatments. Each of these deficiencies result in lost opportunities for providing effective and efficient treatment as well as receiving full reimbursement for the care provided.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to integrating pre-hospital encounters into an EMR. An electronic SBAR tool is provided that guides a clinician to gather demographic information and encounter information. The demographic information associated with one or more patients is received via the SBAR tool. The encounter information is received via the SBAR tool. At least a portion of the demographic information and the encounter information is communicated via the SBAR tool, while in transit via an emergency vehicle, to a healthcare facility. The demographic information and the encounter information are integrated into an EMR associated with each patient.

BRIEF DESCRIPTION OF THE SEVERAL VIEWS OF THE DRAWINGS

The present invention is described in detail below with reference to the attached drawing figures, wherein:

FIGS. 4-7 depict illustrative screen displays, in accordance with embodiments of the present invention.

DETAILED DESCRIPTION

Figure 1:
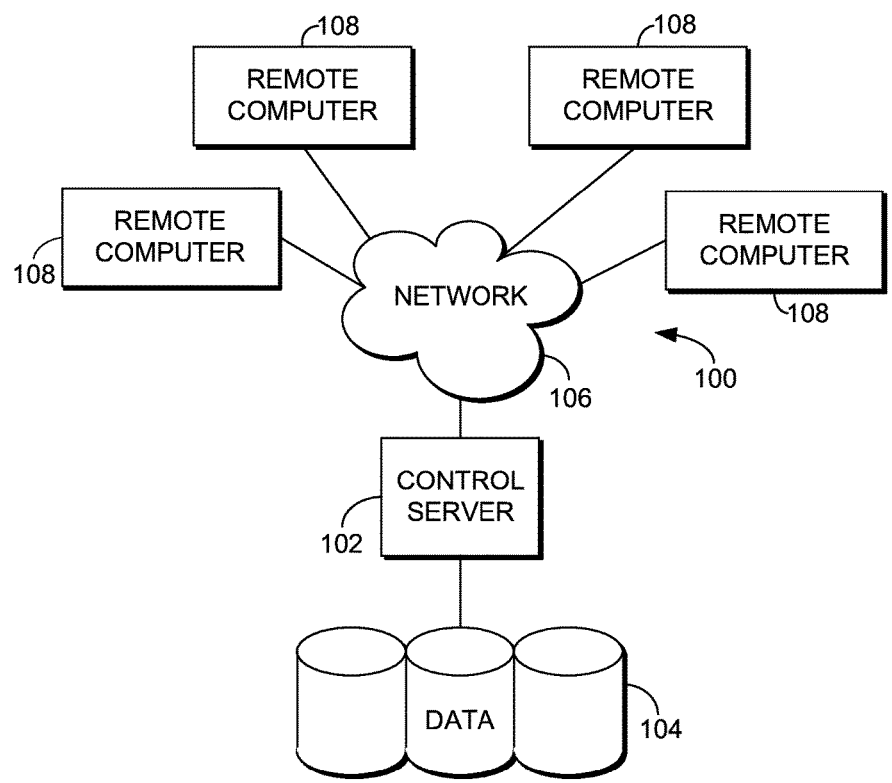
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention capture previously missing pieces of a population's health. Many patients are transported to hospitals via emergency vehicles (e.g., ambulances and helicopters). The information captured in these vehicles is fractured and does not end up directly in the EMR. Further, there is not an electronic version of the SBAR communication tool that integrates into the EMR.

Accordingly, in one aspect, an embodiment of the present invention is directed to a method for integrating pre-hospital encounters into an EMR. The method includes providing an electronic SBAR tool that guides a clinician to gather demographic information and encounter information. The method further includes receiving the demographic information associated with one or more patients via the SBAR tool. The encounter information is received via the SBAR tool. At least a portion of the demographic information and the encounter information is communicated via the SBAR tool, while in transit via an emergency vehicle, to a healthcare facility.

In another aspect of the invention, an embodiment is directed to a graphical user interface (GUI). The GUI comprises a patient demographics display area that displays one or more links to tools that guide a clinician to gather demographic information and encounter information for a patient. An encounter display area displays encounter tools configured to receive encounter information. A SBAR display area displays an editable SBAR form that is communicated, while in transit, to a healthcare facility.

In a further aspect, an embodiment is directed to system environment for integrating pre-hospital encounters in an EMR. The system includes an SBAR component that provides an SBAR tool that guides a clinician to gather demographic information and encounter information. A receiving component receives demographic information and encounter information associated with one or more patients via the SBAR tool. A communication component communicates via the SBAR tool, while in transit via an emergency vehicle, at least a portion of the demographic information and the encounter information to a healthcare facility and enables two-way communication between the SBAR tool and the healthcare facility. An integration component integrates the demographic information and encounter information into an EMR associated with each patient. An ancillary information component receives ancillary information. The ancillary information comprises weather information, traffic information, traffic signal information, and environment information that affects an estimated time of arrival. The ancillary information further calculates the estimated time of arrival based on the ancillary information. A protocol component provides an actionable protocol based on the encounter information and the ancillary information and receives a response or dismissal of an action associated with the actionable protocol. The response or dismissal includes a justification. A time limit component receives a time limit associated with the actionable protocol.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, ambulatory settings, medical billing and financial offices, hospital administration settings, home healthcare environments, clinicians' offices, Center for Disease Control, Centers for Medicare & Medicaid Services, World Health Organization, any governing body either foreign or domestic, Health Information Exchange, and any healthcare/government regulatory bodies not otherwise mentioned. Clinicians may comprise a treating physician or physicians; specialists such as intensivists, surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
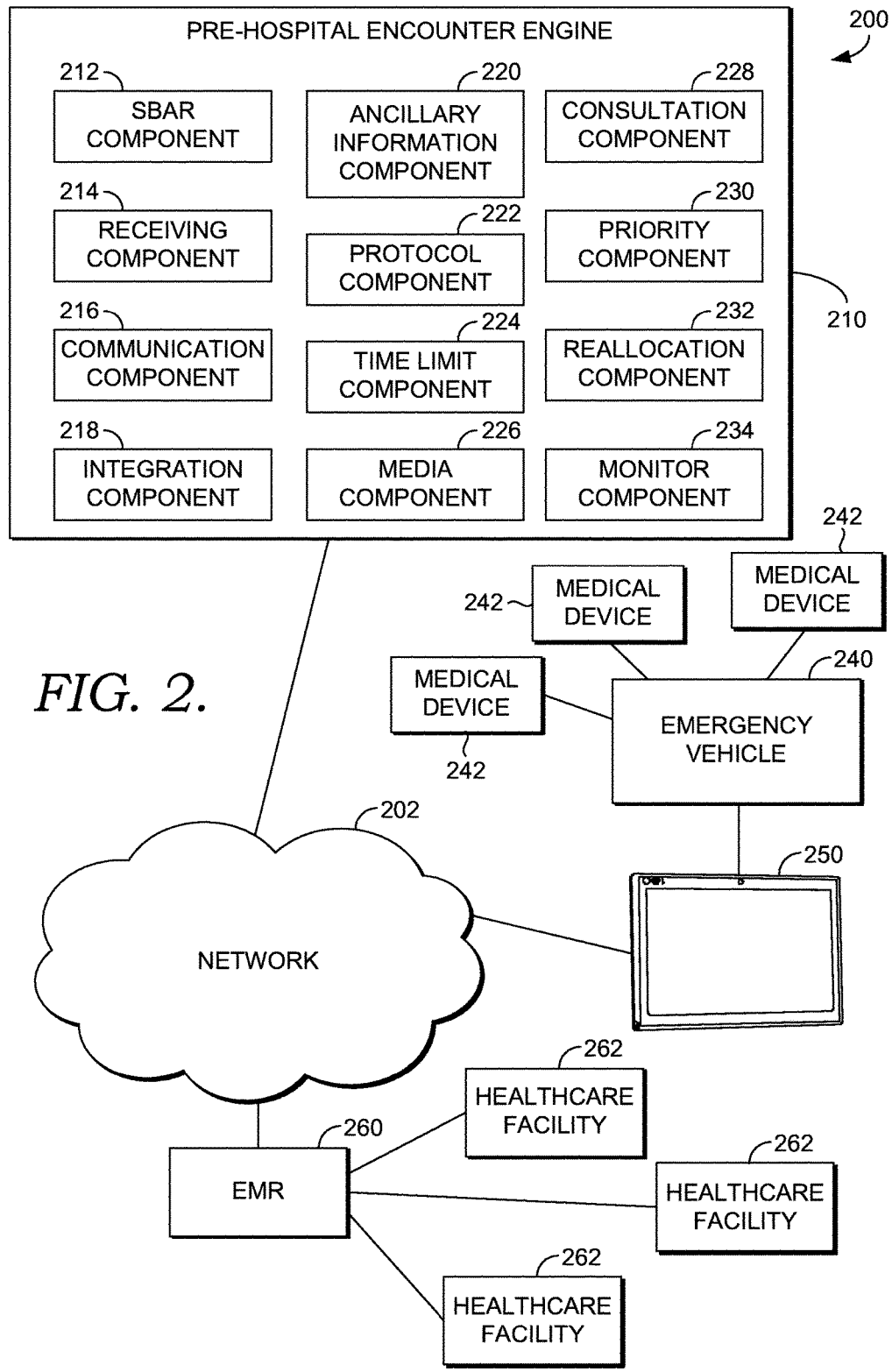
FIG. 2 is a block diagram of an exemplary system including a pre-hospital encounter engine, in accordance with an embodiment of the present invention.

Turning now to FIG. 2, an exemplary computing system environment 200 is depicted suitable for use in implementing embodiments of the present invention. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes a display device 250 (e.g., dashboard, computer, mobile device, and the like) associated with an emergency vehicle 240, one or more medical devices 242 associated with the emergency vehicle 240, pre-hospital encounter engine 210, EMR 260, and one or more healthcare facilities 262, all in communication with one another via a network 202. The network 202 may include, without limitation, one or more secure local area networks (LANs) or wide area networks (WANs). The network 202 may be a secure network associated with a facility such as a healthcare facility. The secure network 202 may require that a user log in and be authenticated in order to send and/or receive information over the network 202.

In some embodiments, one or more of the illustrated components/modules may be implemented as stand-alone applications. In other embodiments, one or more of the illustrated components/modules may be distributed across multiple pre-hospital encounter engines 210. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the pre-hospital encounter engines 210 might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The EMR 260 is configured to provide information to and store information communicated by, for example, the pre-hospital encounter engine 210. The information stored in association with the EMR 260 is configured to be searchable for one or more items of information stored in association therewith. The information stored in association with the EMR 260 may comprise information received from or used by various components of the pre-hospital encounter engine.

The EMR 260 may store EMRs of patients associated with one or more healthcare facilities. EMRs may comprise electronic clinical documents such as images, clinical notes, orders, summaries, reports, analyses, information received from pre-hospital encounter engine 210 and medical devices 242, or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, clinician assignments, and a host of other relevant clinical information.

The content and volume of such information in the EMR 260 is not intended to limit the scope of embodiments of the present invention in any way. Further, though illustrated as a single, independent component, the EMR 260 may, in fact, include a plurality of applications and/or storage devices, for instance, a database cluster.

The display device 250 may be any type of display device capable of communicating via the network 202 with the pre-hospital encounter engine 210, the EMR 260, the healthcare facilities 262, or the medical devices 242. Such devices may include any type of mobile and portable devices including cellular telephones, personal digital assistants, tablet PCs, smart phones, and the like.

The display of the display device 250 is configured to display information to the user of the display device 250 (i.e., an emergency responder). The information may include communications initiated by and/or received by the pre-hospital encounter engine 210. Embodiments are not intended to be limited to visual display but rather may also include audio presentation, visual presentation, combined audio/visual presentation, and the like.

Components of the pre-hospital encounter engine 210 may include a processing unit, internal system memory, and a suitable system bus for coupling various system components, including one or more data stores for storing information (e.g., files and metadata associated therewith). The pre-hospital encounter engine 210 typically includes, or has access to, a variety of computer-readable media.

The computing system environment 200 is merely exemplary. While the pre-hospital encounter engine 210 is illustrated as a single unit, it will be appreciated that the pre-hospital encounter engine 210 is scalable. For example, the pre-hospital encounter engine 210 may in actuality include a plurality of computing devices in communication with one another. The single unit depictions are meant for clarity, not to limit the scope of embodiments in any form.

As shown in FIG. 2, the pre-hospital encounter engine 210 comprises, in various embodiments an SBAR component 212, a receiving component 214, a communication component 216, an integration component 218, an ancillary information component 220, a protocol component 222, a time limit component 224, a media component 226, a consultation component 228, a priority component 230, a reallocation component 232, and a monitor component 234. In some embodiments, one or more of the components may be implemented as stand-alone applications. It will be understood that the components illustrated in FIG. 2 are exemplary in nature and in number and should not be construed as limiting. Any number of components may be employed to achieve the desired functionality within the scope of embodiments hereof.

SBAR component 212 provides an SBAR tool that guides a clinician to gather demographic information and encounter information. The SBAR tool provides various tools that enable the clinician to capture information relevant to the particular situation. Receiving component 214 receives demographic information and encounter information associated with one or more patients via the SBAR tool and associated tools. For example, tools may include a keyboard tool to document the encounter, a subjective-objective-assessment-plan (SOAP) narrative tool to create SOAP notes for the encounter, a Broselow tool to quickly identify correct dosage of medication and equipment sizes, an Revised Trauma Score (RTS) scoring tool to triage the patient while in transit to the healthcare facility, a Parkland formula tool to provide an indication of a burn percentage of a patient via a rule of 9's tool that calculates the appropriate amount of resuscitation fluid needed by the patient. Additional encounter tools may include a drug calculator tool, a drug look up tool, a call information tool a medications and allergies tool, a Glasgow Coma Scale (GCS) tool, a treatments and procedures tool, a transmit tool that transmits information to the healthcare facility, a forms tool that provides forms to the patient in advance of the patient's arrival at the healthcare facility, and a photographs tool that captures and communicates photographs of the patient to the healthcare facility.

Communication component 216 communicates via the SBAR tool, while in transit via an emergency vehicle, at least a portion of the demographic information and the encounter information to a healthcare facility. The information may be communicated directly to the healthcare facility or to an EMR associated with the patient accessible by the healthcare facility. Communication component 216 further enables two-way communication between the SBAR tool and the healthcare facility. Encounter information may further be provided by the one or more medical devices 242. In one embodiment, monitor component 234 monitors equipment (e.g., medical devices) in the emergency vehicle. Monitor component 234 may communicate medical device information directly to the pre-hospital encounter engine 210, the EMR 260, or the healthcare facility 262.

Integration component 218 integrates the demographic information and the encounter information into an EMR associated with each patient. Integration component 218 may communicate the demographic information and the encounter information via the network 202 to the EMR 260 or to a healthcare facility 262. Integration component 218 enables information that may otherwise be lost during an emergency encounter to be documented and charted in the EMR. In so doing, integration component 218 prevents repeated work or care from being provided because documentation regarding such pre-hospital work is readily accessible to the clinicians treating the patient at the healthcare facility (e.g., hospital).

Ancillary information component 220 receives ancillary information. The ancillary information may comprise weather information, traffic information, traffic signal information, and environment information and may affect an estimated time of arrival. The ancillary information component 220 calculates the estimated time of arrival based on the ancillary information. For example, ancillary information component 220 may receive ancillary information that indicates construction will delay an emergency vehicle headed to a particular healthcare facility. The delay may cause the ancillary information component 220 to reroute the emergency vehicle to a different healthcare facility, alter the path the emergency vehicle travels to the particular healthcare facility, identify and request additional resources (e.g., a different type of emergency vehicle) that can arrive faster or in a more timely manner than the current emergency vehicle, or determine the clinician associated with the particular emergency vehicle should perform a particular action (i.e., actionable protocol) based on the delay or estimated time or arrival.

Protocol component 222 provides an actionable protocol based on the encounter information and the ancillary information. Protocol component 222 further receives a response or dismissal of an action associated with the actionable protocol. The response or dismissal may include a justification. This may enable a healthcare facility or clinician to be reimbursed for the actionable protocol if a particular action related to the actionable protocol is not able to be performed or the patient refuses the action. Time limit component 224 receives a time limit associated with the actionable protocol. The time limit may be related to a required amount of time a particular action must be performed relative to a particular event or another action.

In one embodiment, media component 226 receives physical pictures and/or video of the patient via the SBAR tool. Media component 226 may communicate the physical pictures and/or video to the healthcare facility via the communication component 216. In one embodiment, consultation component 228 enables a clinician consultation via the SBAR tool. The communication component 216 may provide the two-way communication necessary for the consultation. The consultation enables a remote clinician (e.g., healthcare facility or primary care clinician) to provide a consultation for the patient.

In one embodiment, priority component 230 prioritizes patients for the healthcare facility based on the encounter information and the ancillary information. The priority allows the healthcare facility to triage and prepare for patients arriving by emergency vehicles. In one embodiment, reallocation component 232 reallocates resources for a patient in trauma. Resources may be reallocated based on priority or based on specific information associated with the encounter information.

Figure 3:
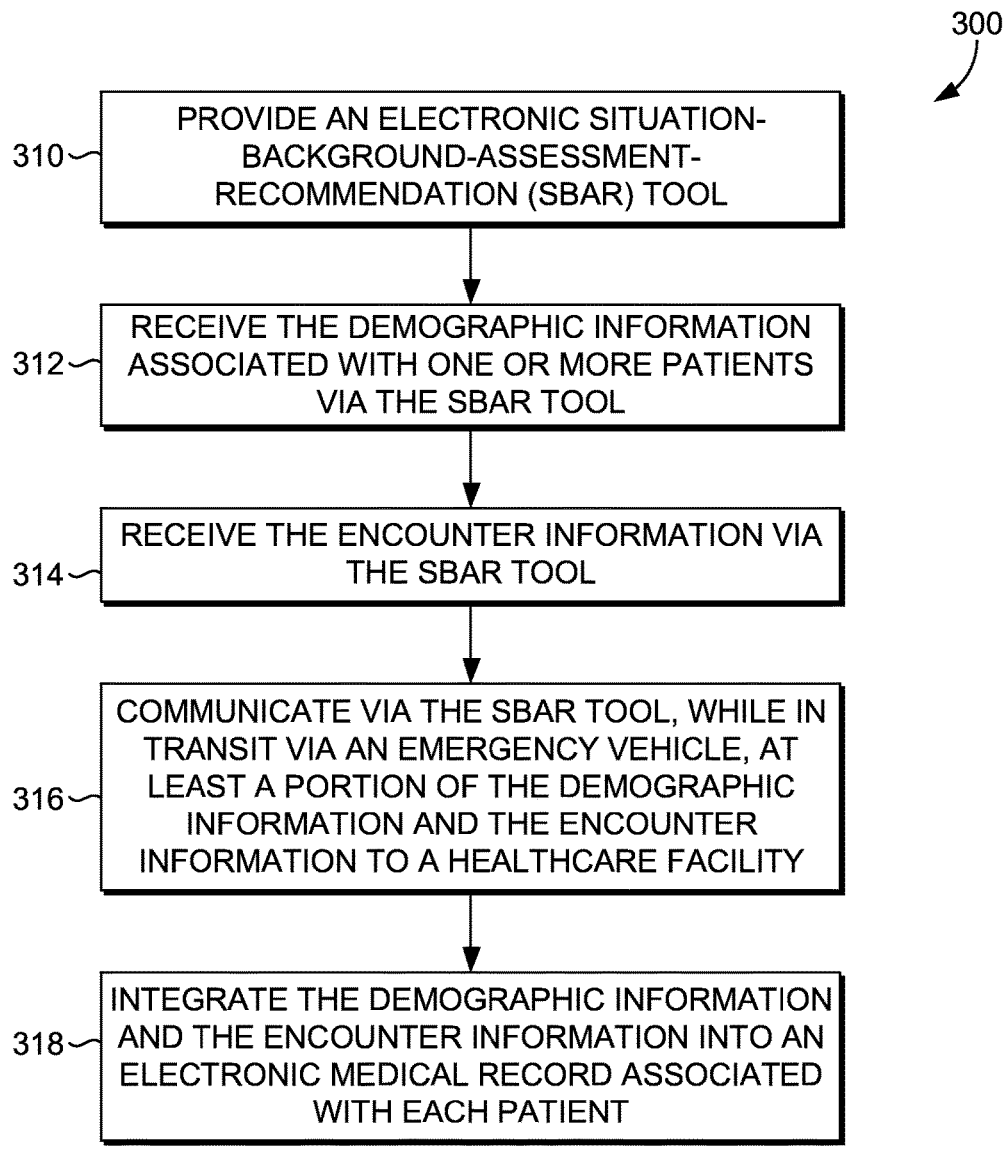
FIG. 3 is a flow diagram showing an exemplary method for integrating pre-hospital encounters into an EMR, in accordance with various embodiments of the present invention.

Turning now to FIG. 3, a flow diagram is provided illustrating a method 300 for integrating pre-hospital encounters into an EMR, in accordance with an embodiment of the present invention. Initially, as shown at step 310, an electronic SBAR tool is provided that guides a clinician to gather demographic information and encounter information. Demographic information associated with one or more patients is received, at step 312, via the SBAR tool. The encounter information is received via the SBAR tool at step 314. At least a portion of the demographic information and the encounter information is communicated via the SBAR tool, at step 316, while in transit via an emergency vehicle, to a healthcare facility. At step 318, the demographic information and the encounter information is integrated into an EMR associated with each patient. In one embodiment, patients are prioritized for the healthcare facility based on the encounter information and the ancillary information. In one embodiment, resources are reallocated for a patient in trauma. For example, the healthcare facility is able to utilize the information integrated into each patient's EMR to prepare resources that may be required by each patient. In one embodiment, the SBAR tool monitors equipment in the emergency vehicle and may communicate any information received from the equipment to the EMR, the healthcare facility, or a clinician associated with the healthcare facility.

In one embodiment, ancillary information is received by the SBAR tool. The ancillary information may comprise weather information, traffic information, traffic signal information, and environment information. The ancillary information may affect an estimated time of arrival of the emergency vehicle at the healthcare facility. For example, heavy traffic, malfunctioning traffic signals, or bad weather may cause delays in the arrival time. Similarly, environment information, such as criminal activity in the area, may also cause delays in the arrival time. The SBAR tool utilizes the received ancillary information, in one embodiment, to calculate the estimated time of arrival. The estimated time of arrival may influence recommendations or actionable protocols provided by the SBAR tool.

In one embodiment, two-way communication between the SBAR tool and the healthcare facility is enabled. The two-way communication may provide the healthcare facility with additional information necessary to prepare for the arrival of the patient. The two-way communication may additionally provide the clinicians associated with the emergency vehicle information that may assist the clinicians in providing care to the patient. In one embodiment, physical pictures and/or video of the patient is received via the SBAR tool. In one embodiment, the physical pictures and/or video is communicated, via the SBAR tool, to the healthcare facility. In one embodiment, a clinician consultation is enabled via the SBAR tool, enabling a clinician not physically located in the emergency vehicle to provide a consultation for the patient. For example, the clinician may physically be located at the healthcare facility awaiting the patient. The clinician may be the primary care physician associated with or a clinician that has previously provided care for the patient.

In one embodiment, an actionable protocol based on the encounter information and the ancillary information is provided via the SBAR tool. The actionable protocol may instruct a clinician to perform action or a series of actions. The actions are charted within the SBAR tool and communicated to the EMR, enabling the care provided while in the emergency vehicle to be reimbursed. In one embodiment, a response or dismissal of an action associated with the actionable protocol is received. The response or dismissal may include a justification. For example, the protocol may require the clinician to chart the blood pressure of the patient. In order to be reimbursed, the clinician may be required to follow the protocol. However, if the patient has no arms or refuses care, the clinician may dismiss the action associated with the blood pressure, provide the justification for dismissing the action, and proceed to the next action.

In one embodiment, a time limit associated with the actionable protocol is received. The time limit is utilized by the SBAR tool to provide a record of the time required to perform actions associated with the actionable protocol. Performing the actions within the time limit may affect reimbursement and because the SBAR tool is able to confirm whether the time limits are met, the SBAR tool may maximize and streamline the reimbursement process.

Figure 4:
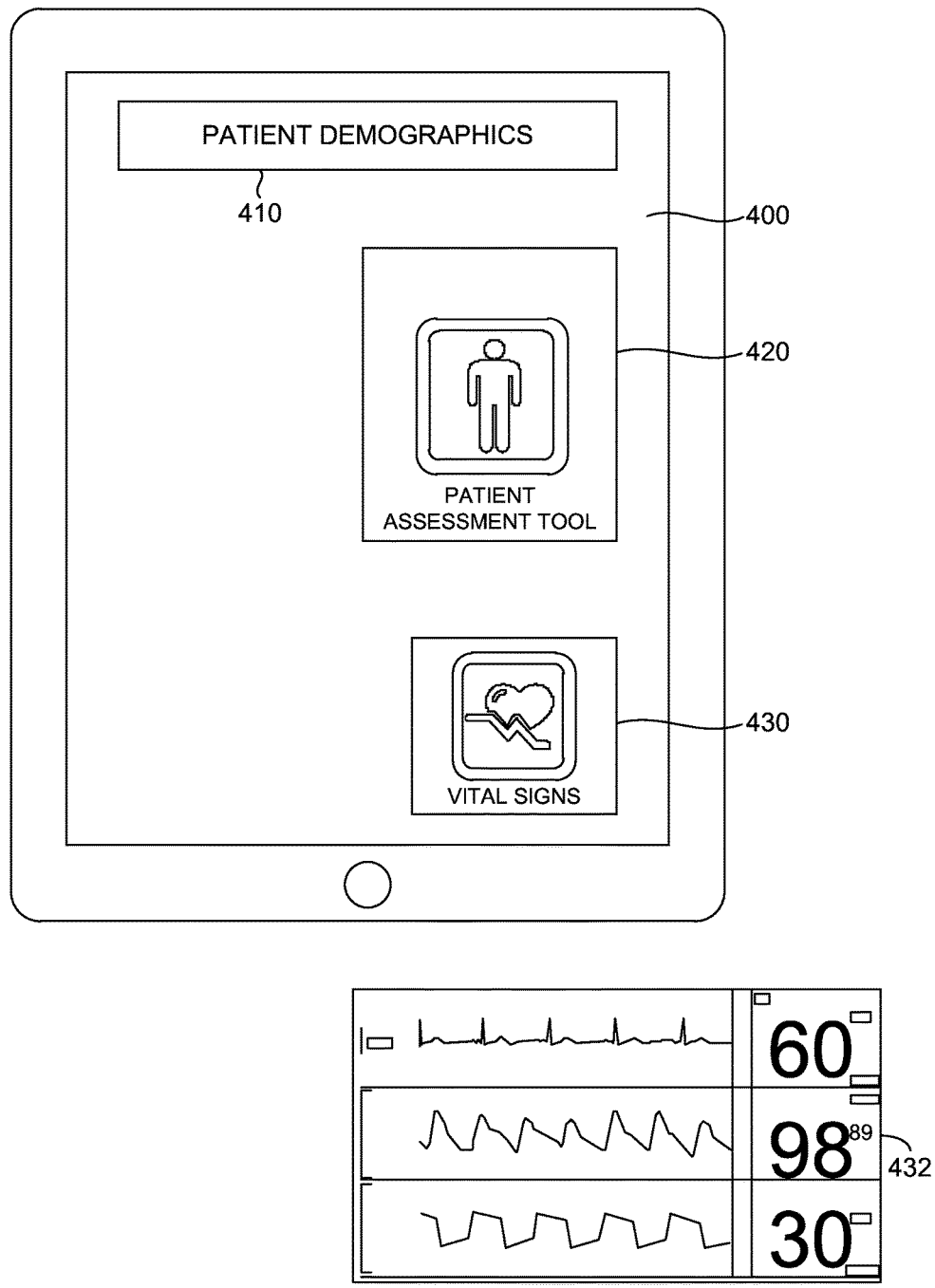
Figure 5:
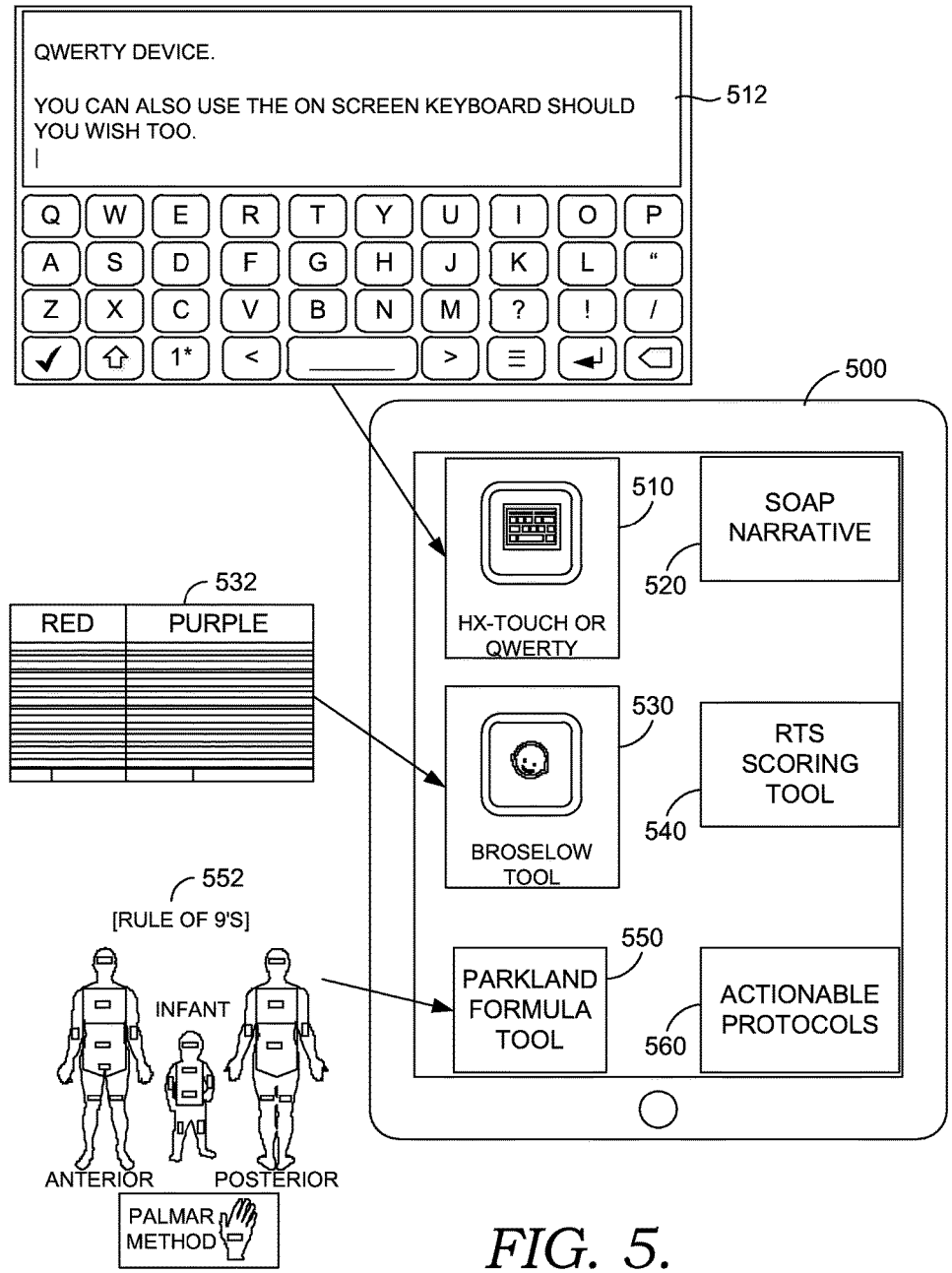
Figure 6:
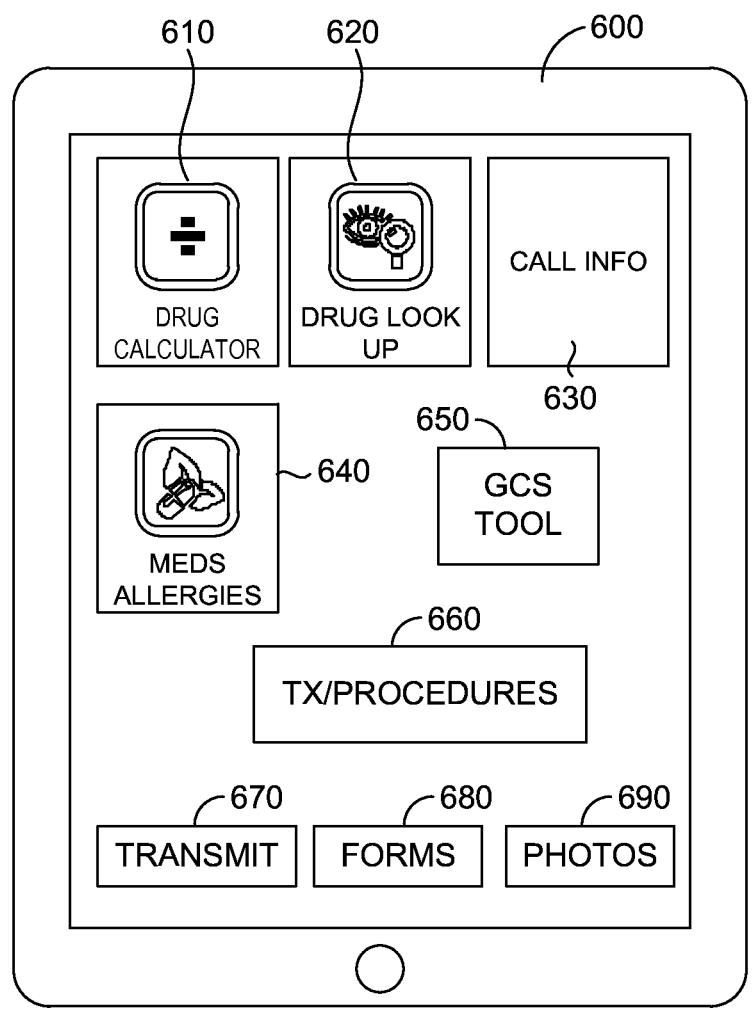

With reference to FIGS. 4-6, illustrative screen displays for integrating pre-hospital encounters into an EMR are provided. It is understood that each of the illustrative screen displays are connected logically, such that they comprise a user interface designed for integrating pre-hospital encounters into an EMR. The screen displays may appear in any order and with any number of screen displays, without regard to whether the screen display is described or depicted herein. The screen displays provide tools that enable pre-hospital encounters to be integrated into EMR.

Referring now to FIG. 4, an illustrative screen display 400 of an embodiment of the present invention is shown. A patient demographics display area 400 that displays one or more links 410, 420, 430 to tools that guide a clinician to gather demographic information and encounter information for a patient. The link 410 to the patient demographics tool enables the clinician to launch a tool that receives demographics information associated with the patient. The link 420 to the patient assessment tool enables the clinician to launch one or more tools that receive assessment information associated with the patient. Similarly, the link 430 to the vital signs tool provides the clinician with the current vital signs 432 of the patient.

Turning now to FIGS. 5 and 6, illustrative screen displays 500, 600 of embodiments of the present invention are shown. Encounter display area 500 displays encounter tools configured to receive encounter information. The encounter tools may include a keyboard tool 510 that opens a keyboard 512 allowing the clinician to document. A SOAP narrative tool 520 enables the clinician to create SOAP notes for the encounter. A Broselow tool 530 enables the clinician to open an electronic version of the Broselow tape 532 to quickly identify correct dosage of medication and equipment sizes. An RTS scoring tool 540 provides the clinician an electronic physiologic scoring system to triage the patient while in transit to the healthcare facility. The RTS may also be communicated to the healthcare facility to allocate resources to a patient in trauma, prior to the arrival of the patient. A Parkland formula tool 550 enables the clinician to electronically provide an indication of a burn percentage of a patient via a rule of 9's tool 552 and calculate the appropriate amount of resuscitation fluid needed by the patient.

Encounter display area 600 displays additional encounter tools configured to receive encounter information. The additional encounter tools may include: a drug calculator tool 610, a drug look up tool 620, a call information tool 630, a medications and allergies tool 640, a GCS tool 650, a treatments and procedures tool 660, a transmit tool 670, a forms tool 680, and a photographs tool 690. The transmit tool 670 enables the clinician to transmit demographic information and/or encounter information to the healthcare facility. The forms tool 680 enables the clinician to provide forms to the patient in advance of the patient's arrival at the healthcare facility. The forms tool 680 may also receive required signatures form the patient for the various forms. The photographs tool 690 enables the clinician to capture and communicate photographs of the patient to the healthcare facility.

In FIG. 7, an illustrative screen display 700 of an embodiment of the present invention is shown. A SBAR display area displays an editable SBAR form that is communicated, while in transit, to a healthcare facility. The SBAR form enables the clinician to document the situation 710 and any concerns 712 regarding the patient's status. The SBAR form further enables the clinician to document and/or review the patient's background 720, including the most recent and/or previous vital signs. Still further, the SBAR form enables the clinician to provide an assessment 730 of the patient and provide an indication of potential problems 732 affecting the patient. The SBAR form also enables the clinician to provide a recommendation 740 for the patient. The recommendation may be made from a dropdown menu 750 or from a list of common protocols 754.

Figure 8:
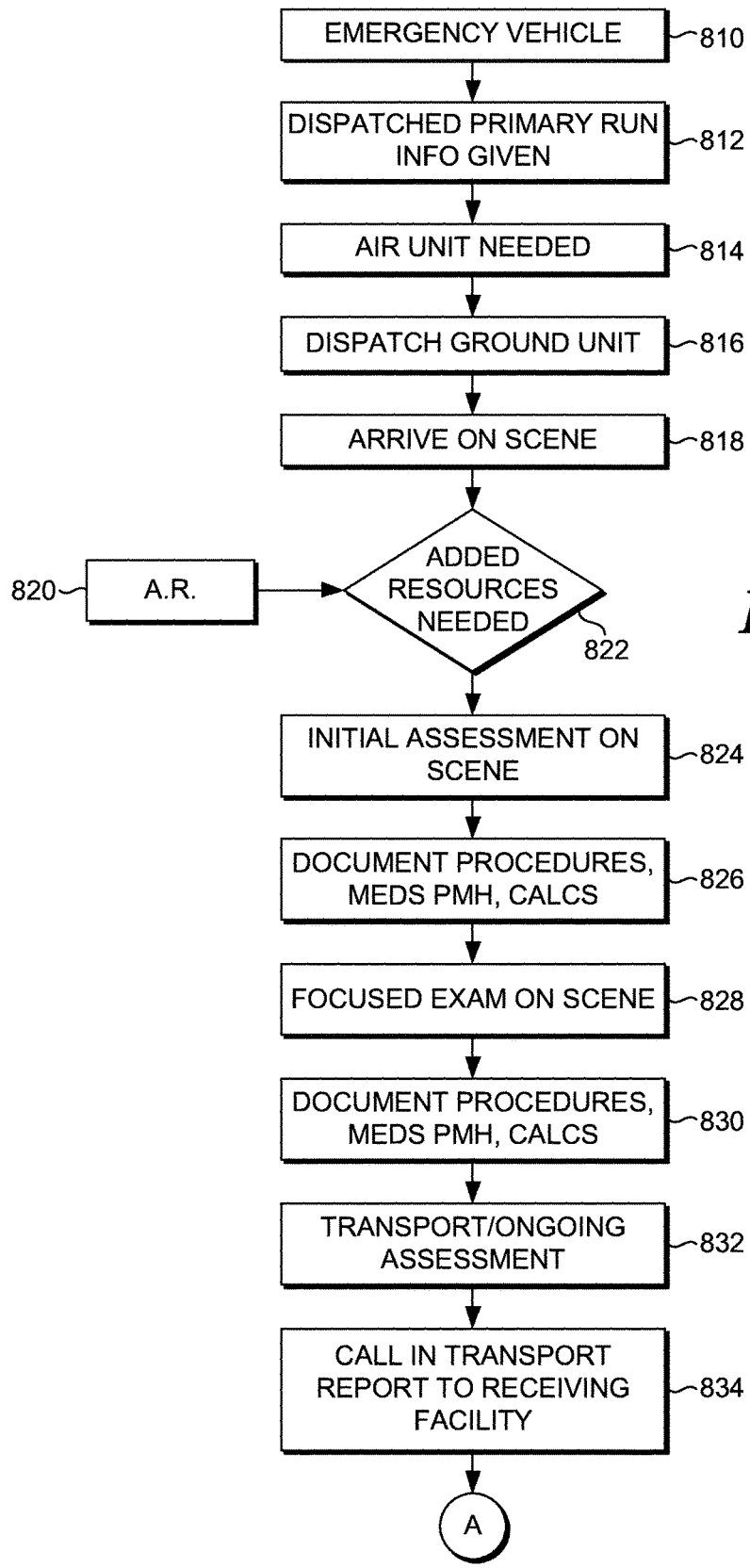
FIG. 8 is a flow diagram showing an exemplary method for integrating pre-hospital encounters into an EMR, in accordance with various embodiments of the present invention.
Figure 8:
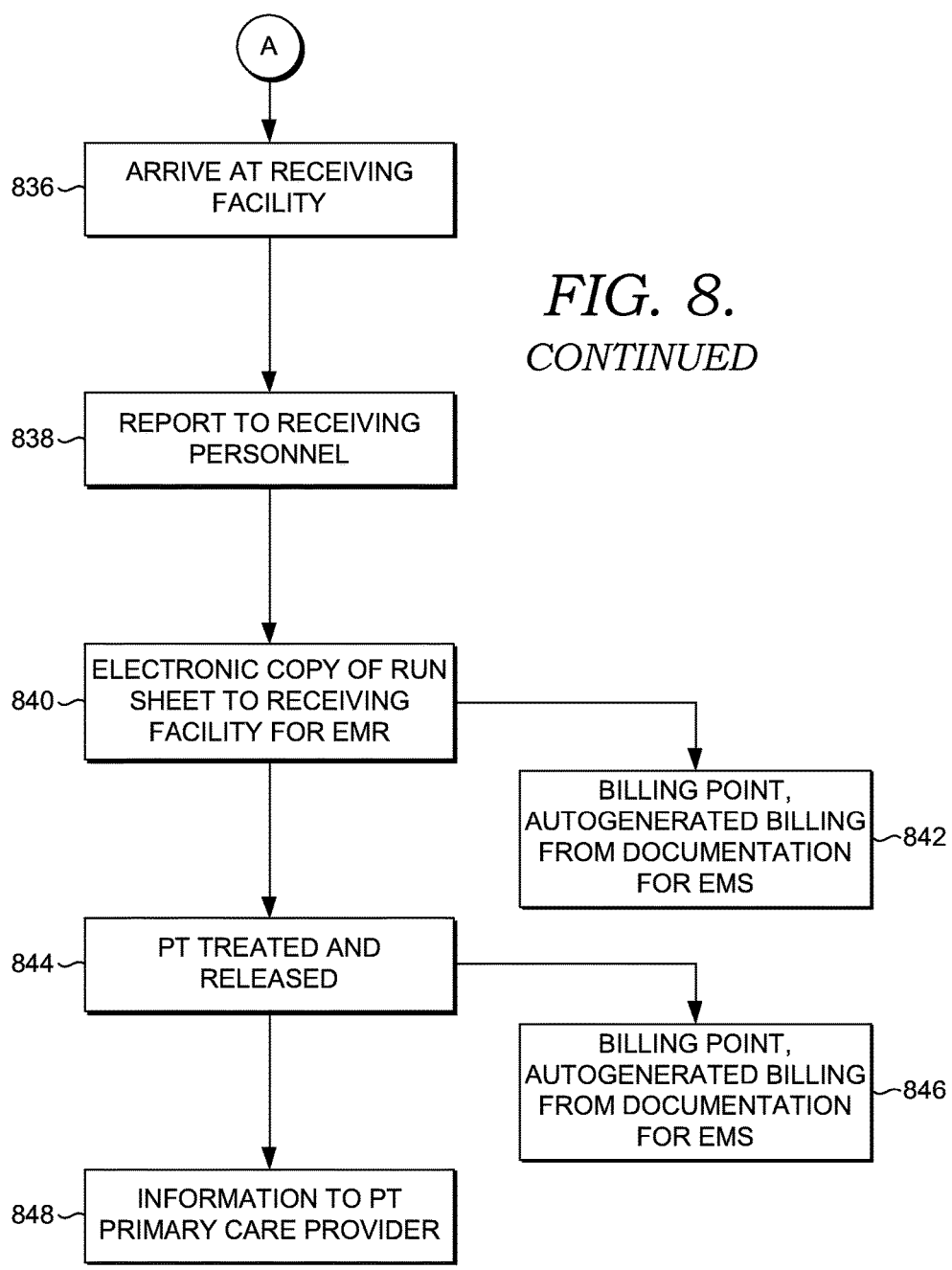

Referring now to FIG. 8, a flow diagram is provided illustrating a method 800 for integrating pre-hospital encounters into an EMR, in accordance with an embodiment of the present invention. Initially, as shown at step 810, an emergency vehicle is contacted. Information is provided to the emergency vehicle, at step 812. At step 814, a decision is made whether an air unit is needed. A ground unit is dispatched at step 816. The emergency vehicle arrives on the scene at step 818. At step 820, an automatic response determines what resources will respond to a given scenario and resources are added, if necessary, at step 822.

An initial assessment is provided at the scene utilizing the SBAR tool, at step 824. Procedures, medications, and past medical history are documented via the SBAR tool, at step 826, based on the initial assessment. A more focused examination is then provided, at step 828, utilizing the SBAR tool. Procedures, medications, and past medical history are documented via the SBAR tool, at step 830, based on the more focused examination. At step 832, a transport/ongoing assessment is prepared. The assessment is communicated, via the SBAR tool, to a receiving healthcare facility at step 834.

Still referring to FIG. 8, the emergency vehicle arrives at the receiving healthcare facility at step 836. Report is given to receiving personnel at step 838. An electronic version of the run sheet is communicated via the SBAR tool, at step 840, to the receiving healthcare facility and integrated into the patient's EMR. Billing is autogenerated based on the information communicated by the SBAR tool at step 842. After the patient is treated and released at step 844, billing is autogenerated again, at step 846, based on additional information received by the patient's EMR. Information regarding the pre-hospital encounter is provided to the patient's primary care provider at step 848.

As can be understood, the present invention provides systems, methods, and user interfaces for providing clinical decision support based on a patient's clinical situation. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more non-transitory computer storage media having computer-executable instructions embodied thereon, that when executed, perform a method for directly updating an electronic medical record (EMR) with pre-hospital demographic information and encounter information in an emergency situation, the method comprising:
providing an electronic Situation-Background-Assessment-Recommendation (SBAR) tool at a first computing device present at the emergency situation, wherein the SBAR tool enables a clinician to gather demographic information and encounter information;
receiving the demographic information and encounter information associated with one or more patients via the SBAR tool;
communicating via the SBAR tool, while in transit via an emergency vehicle, at least a portion of the demographic information and the encounter information to a healthcare facility;
directly updating, via the SBAR tool the demographic information and the encounter information into an EMR associated with the one or more patients;
receiving ancillary information via the SBAR tool;
calculating, in real time, an estimated time of arrival based on the ancillary information;
providing an actionable protocol based, at least, on the estimated time of arrival; and
using the ancillary information, the encounter information, and information on the actionable protocol to prioritize care for the one or more patients at the healthcare facility.

2. The media of claim 1, wherein the ancillary information at least comprises weather information, traffic information, traffic signal information, and environment information that affects the estimated time of arrival.

3. The media of claim 1, further comprising enabling two-way communication between the SBAR tool and the healthcare facility.

4. The media of claim 1, further comprising receiving a response or dismissal of an action associated with the actionable protocol, the response or dismissal including a justification.

5. The media of claim 1, further comprising receiving physical pictures and/or video of the patient via the SBAR tool.

6. The media of claim 5, further comprising communicating the physical pictures and/or video to the healthcare facility via the SBAR tool.

7. The media of claim 1, further comprising enabling a clinician consultation via the SBAR tool.

8. The media of claim 1, further comprising receiving a time limit associated with the actionable protocol.

9. The media of claim 8, further comprising reallocating resources for a patient in trauma.

10. The media of claim 1, further comprising monitoring equipment in the emergency vehicle.

11. The media of claim 1, wherein the encounter information is collected via one or more encounter tools of the SBAR tool, the one or more encounter tools including: a subjective-objective-assessment-plan (SOAP) narrative tool to create notes for the emergency situation, a Broselow tool to identify correct medication dosage and equipment size, a Revised Trauma Score (RTS) scoring tool to triage the patient while in transit to the healthcare facility, a Parkland formula tool to provide an indication of a burn percentage of the patient, an actionable protocols tool to provide one or more actionable protocols based on the encounter information and the ancillary information, a drug calculator tool, a drug look up tool, a call information tool, a medications and allergies tool, a Glasgow Coma Scale (GCS) tool to measure the conscious state of the patient, a treatments and procedures tool, a transmit tool to transmit information to the healthcare facility, a forms tool to provide one or more forms to the patient in advance of the patient's arrival at the healthcare facility, and a photographs tool to capture and communicate photographs of the patient to the healthcare facility.

12. The system of claim 11, wherein billing is autogenerated based on information communicated by the SBAR tool at a time of emergency treatment and again at a time of patient release, once additional information on patient treatment is available at each EMR associated with each patient.

13. One or more non-transitory computer storage media having computer-executable instructions embodied thereon that, when executed by one or more computing devices, cause the one or more computing devices to produce a graphical user interface (GUI) for directly updating an electronic medical record (EMR) with pre-hospital demographic information and encounter information in an emergency situation, the GUI comprising:
   a patient demographics display area that displays one or more links to tools that enable a clinician to gather demographic information and encounter information for a patient;
   an encounter display area that displays one or more encounter tools that enable the clinician to enter and retrieve the encounter information; and
   a Situation-Background-Assessment-Recommendation (SBAR) display area that displays an editable SBAR form that is communicated, while in transit, to a healthcare facility, wherein the SBAR form:
   communicates, via the SBAR form and while in transit via an emergency vehicle, at least a portion of the demographic information and the encounter information to a healthcare facility;
   directly updates the demographic information and the encounter information into an EMR associated with the patient;
   receives ancillary information;
   calculates, in real time, the estimated time of arrival for the emergency vehicle based on the ancillary information;
   provides an actionable protocol based, at least, on the estimated time of arrival; and
   prioritizes care for the one or more patients at the healthcare facility using the ancillary information, the encounter information, and information on the actionable protocol.

14. The GUI of claim 13, wherein the encounter tools include a subjective-objective-assessment-plan (SOAP) narrative tool to create notes for the emergency situation, a Broselow tool to identify correct medication dosage and equipment size, a Revised Trauma Score (RTS) scoring tool to triage the patient while in transit to the healthcare facility, a Parkland formula tool to provide an indication of a burn percentage of the patient, an actionable protocols tool to provide one or more actionable protocols based on the encounter information and the ancillary information, a drug calculator tool, a drug look up tool, a call information tool, a medications and allergies tool, a Glasgow Coma Scale (GCS) tool to measure the conscious state of the patient, a treatments and procedures tool, a transmit tool to transmit information to the healthcare facility, a forms tool to provide one or more forms to the patient in advance of the patient's arrival at the healthcare facility, and a photographs tool to capture and communicate photographs of the patient to the healthcare facility.

15. A computer system for directly updating an electronic medical record (EMR) with pre-hospital encounter information and demographic information in an emergency situation associated with one or more patients, the computer system comprising a processor coupled to a non-transitory computer-storage medium, the non-transitory computer-storage medium having stored thereon a plurality of computer software components executable by the processor, the computer software components comprising:
   a Situation-Background-Assessment-Recommendation (SBAR) component that provides an SBAR tool that guides a clinician to gather demographic information and encounter information for the one or more patients beginning at a time of arrival to an emergency site;
   a receiving component that receives the demographic information and the encounter information associated with the one or more patients via the SBAR tool;
   a communication component that communicates via the SBAR tool, while in transit in an emergency vehicle, at least a portion of the demographic information and the encounter information to a healthcare facility, and enables a two-way communication between the SBAR tool and the healthcare facility;
   an integration component that directly updates an EMR associated with each patient with the demographic and the encounter information;
   an ancillary information component that receives ancillary information, the ancillary information comprising weather information, traffic information, traffic signal information, and environment information that affects an estimated time of arrival, and calculates the estimated time of arrival based on the ancillary information;
   a protocol component that provides an actionable protocol based on the encounter information, the estimated time of arrival, and the ancillary information and receives a response or dismissal of an action associated with the actionable protocol, the response or dismissal including a justification;
   a time limit component that receives a time limit associated with the actionable protocol; and
   a priority component that prioritizes patients for the healthcare facility based on the encounter information, information based on the actionable protocol, and the ancillary information; and
   a reallocation component that reallocates resources for a patient in trauma.

16. The system of claim 15, further comprising:
   a media component that receives physical pictures and/or video of the patient via the SBAR tool and communicates the physical pictures and/or video to the healthcare facility; and
   a consultation component that enables a clinician consultation via the SBAR tool.

17. The system of claim 15, further comprising a monitor component that monitors equipment in the emergency vehicle.

18. The system of claim 16, wherein the encounter information is collected via one or more encounter tools of the SBAR tool, the one or more encounter tools including: a subjective-objective-assessment-plan (SOAP) narrative tool to create notes for the emergency situation, a Broselow tool to identify correct medication dosage and equipment size, a Revised Trauma Score (RTS) scoring tool to triage the patient while in transit to the healthcare facility, a Parkland formula tool to provide an indication of a burn percentage of the patient, an actionable protocols tool to provide one or more actionable protocols based on the encounter information and the ancillary information, a drug calculator tool, a drug look up tool, a call information tool, a medications and allergies tool, a Glasgow Coma Scale (GCS) tool to measure the conscious state of the patient, a treatments and procedures tool, a transmit tool to transmit information to the healthcare facility, a forms tool to provide one or more forms to the patient in advance of the patient's arrival at the healthcare facility, and a photographs tool to capture and communicate photographs of the patient to the healthcare facility.

19. The system of claim 18, wherein billing is autogenerated based on information communicated by the SBAR tool at a time of emergency treatment and again at a time of patient release, once additional information on patient treatment is available at each EMR associated with each patient.

\* \* \* \* \*